(12) United States Patent
Kursula et al.

(10) Patent No.: US 10,322,203 B2
(45) Date of Patent: Jun. 18, 2019

(54) AIR FLOW GENERATION FOR SCENT OUTPUT

(71) Applicant: INTEL CORPORATION, Santa Clara, CA (US)

(72) Inventors: Mikko Kursula, Lempaala (FI); Seppo Vesamaki, Tampere (FI); Matti A. Lahdenpera, Tampere (FI); Timo H. Nissinen, Ylojarvi (FI); Marko Vaaranmaa, Lempaala (FI)

(73) Assignee: Intel Corporation, Santa Clara, CA (US)

( * ) Notice: Subject to any disclaimer, the term of this patent is extended or adjusted under 35 U.S.C. 154(b) by 130 days.

(21) Appl. No.: 14/752,655

(22) Filed: Jun. 26, 2015

(65) Prior Publication Data

US 2016/0375170 A1    Dec. 29, 2016

(51) Int. Cl.
*A61L 9/12* (2006.01)
*H04R 1/02* (2006.01)
*A61L 9/14* (2006.01)
*H04R 1/10* (2006.01)

(52) U.S. Cl.
CPC ............... *A61L 9/122* (2013.01); *A61L 9/12* (2013.01); *A61L 9/125* (2013.01); *A61L 9/14* (2013.01); *H04R 1/028* (2013.01); *A61L 2209/111* (2013.01); *H04R 1/1008* (2013.01); *H04R 2499/11* (2013.01)

(58) Field of Classification Search
CPC ...................................... G05B 15/02
USPC ............... 381/332, 334; 239/11; 1/1; 62/436
See application file for complete search history.

(56) References Cited

U.S. PATENT DOCUMENTS

| 2,312,712 | A | | 3/1943 | Hartline |
| 3,640,090 | A | * | 2/1972 | Ares ................. F24F 1/022 62/436 |
| 3,903,726 | A | | 9/1975 | Hirosawa et al. |
| 6,475,658 | B1 | | 11/2002 | Pedicini et al. |
| 2013/0334337 | A1 | * | 12/2013 | Haran ................. A61L 9/14 239/11 |
| 2014/0134053 | A1 | | 5/2014 | Mayer et al. |
| 2014/0275857 | A1 | | 9/2014 | Toth et al. |
| 2014/0334653 | A1 | * | 11/2014 | Luna ................. G05B 15/02 381/332 |
| 2015/0338390 | A1 | | 11/2015 | Anglin, Jr. et al. |

(Continued)

FOREIGN PATENT DOCUMENTS

| JP | 2003098139 A | 4/2003 |
| JP | 2005069742 A | 3/2005 |
| JP | 2014035728 A | 2/2014 |

OTHER PUBLICATIONS

Kursula, Mikko, et al.; U.S. Appl. No. 14/666,622 entitled "Intergrated Gas Sensor" filed Mar. 24, 2015, 40 pages.

(Continued)

*Primary Examiner* — Md S Elahee
(74) *Attorney, Agent, or Firm* — International IP Law Group, P.L.L.C.

(57) ABSTRACT

An apparatus for air flow generation for scent output is described. The device includes a scent system, a speaker, and an output channel. The scent system and the speaker share the output channel, and the speaker is to move air to release scent from the device. A membrane of the speaker may vibrate to produce the air flow.

23 Claims, 7 Drawing Sheets

(56) References Cited

U.S. PATENT DOCUMENTS

2016/0282151 A1* 9/2016 Kursula .............. G01D 11/245
2016/0345083 A1* 11/2016 Pinkerton ................ H04R 1/02

OTHER PUBLICATIONS

PCT International Search Report, PCT Application No. PCT/US2016/017225, dated May 12, 2016, 3 pages.

* cited by examiner

300

400

500

AIR FLOW GENERATION FOR SCENT OUTPUT

TECHNICAL FIELD

The present disclosure relates generally to techniques for scent effects. More specifically, the present techniques relate to scent effects in wearable or mobile devices.

BACKGROUND ART

Mobile devices include small computing devices that typically operate on relatively small amounts of power. These devices may include, but are not limited to, mobile phones, smart phones, wearable devices, tablets, and laptops, etc. Mobile devices support numerous functions, such as communication, social networking, gaming, various data manipulations and computations.

BRIEF DESCRIPTION OF THE DRAWINGS

The same numbers are used throughout the disclosure and the figures to reference like components and features. Numbers in the 100 series refer to features originally found in FIG. 1; numbers in the 200 series refer to features originally found in FIG. 2; and so on.

DESCRIPTION OF THE EMBODIMENTS

Figure 1:
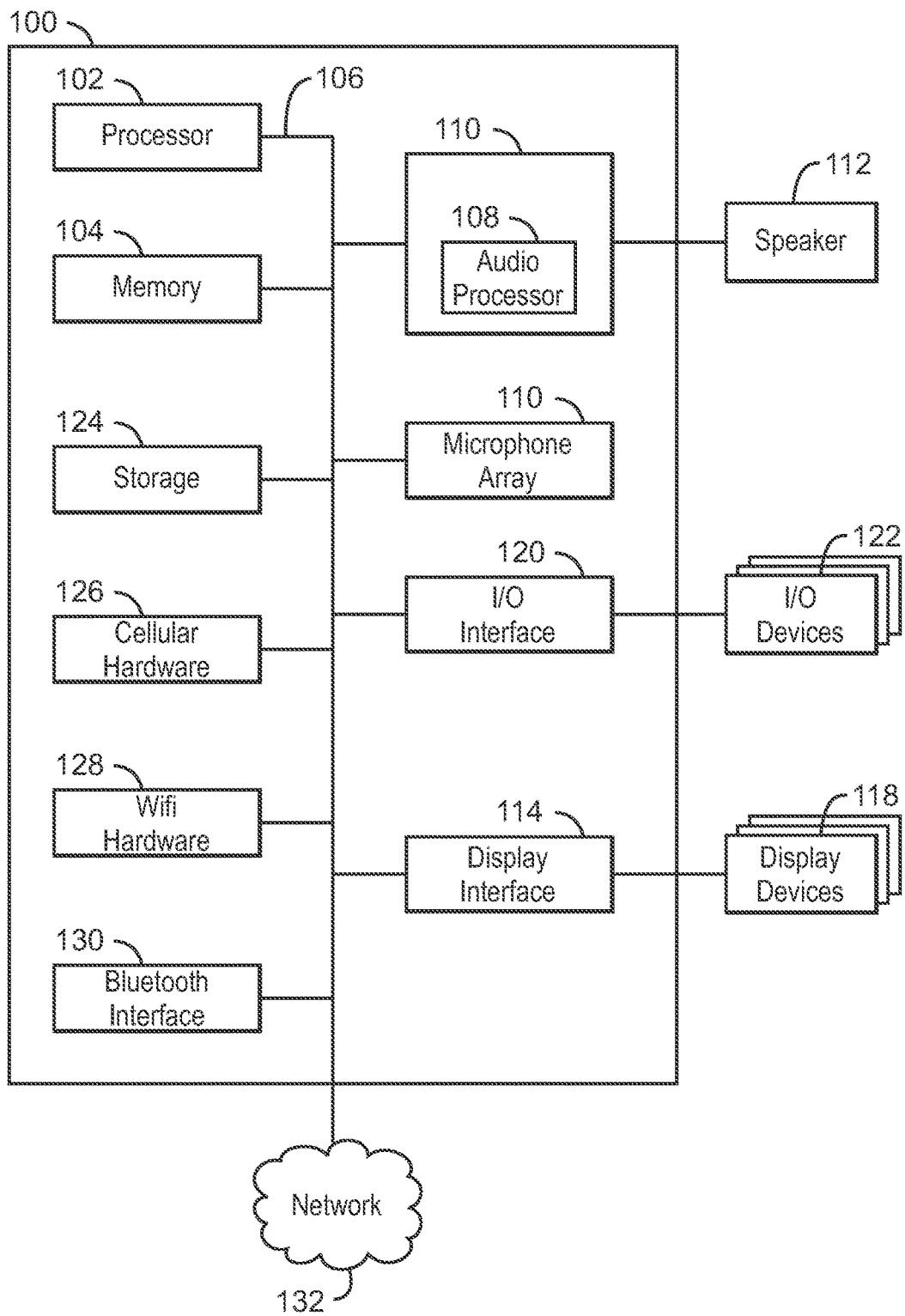
FIG. 1 is a block diagram of an electronic device that enables air flow generation for scent output.

Mobile devices can be used in an endless number of applications. Operation of mobile devices can be supplemented, supported, and/or enhanced through effects that appeal to the senses. The display of a mobile device can be configured to render bright, intense colors that are aesthetically appealing. Many mobile devices include haptic feedback that recreates the sense of touch by applying forces, vibrations, or motions to the user. Mobile devices also include audio systems that output sounds from the mobile device.

Embodiments described herein relate generally to techniques for scent effects in mobile devices. An audio system may include a speaker that generates air flow as a byproduct of sound production. This air flow can be utilized to push scents out of the device. The speaker can be also intentionally used to generate only the airflow without sound output. Scent effects can be released by a scent system of the device, and airflow from the speaker can distribute the scent vapor or gas external to the device.

The device may be operable to generate an electromechanical induced air movement (e.g., via haptic effect, speaker, fan, etc.) such a scent from the scent system is expelled from the device. In embodiments, the device is a speaker membrane which is operable to produce audible sound. In embodiments, the apparatus comprises logic to lower the frequency of an AC (Alternating Current) signal for the speaker membrane such that the speaker membrane vibrates without generating human audible noise. In embodiments, the housing is part of a wearable device. In embodiments, the device is at least one of: a speaker membrane, a vibrating motor, a piezoelectric haptic actuator, a fan, or an air pump. In embodiments, the other device is one of: a smart phone, a tablet PC (Personal Computer), or a wireless communication enabled device such as Wireless Local Area Network (WLAN) enabled device.

In the following description, numerous details are discussed to provide a more thorough explanation of embodiments of the present disclosure. It will be apparent, however, to one skilled in the art, that embodiments of the present disclosure may be practiced without these specific details. In other instances, well-known structures and devices are shown in block diagram form, rather than in detail, in order to avoid obscuring embodiments of the present disclosure.

Note that in the corresponding drawings of the embodiments, signals are represented with lines. Some lines may be thicker, to indicate more constituent signal paths, and/or have arrows at one or more ends, to indicate primary information flow direction. Such indications are not intended to be limiting. Rather, the lines are used in connection with one or more exemplary embodiments to facilitate easier understanding of a circuit or a logical unit. Any represented signal, as dictated by design needs or preferences, may actually comprise one or more signals that may travel in either direction and may be implemented with any suitable type of signal scheme.

Throughout the specification, and in the claims, the term "connected" means a direct electrical, mechanical, or magnetic connection between the things that are connected, without any intermediary devices. The term "coupled" means either a direct electrical, mechanical, or magnetic connection between the things that are connected or an indirect connection through one or more passive or active intermediary devices. The term "circuit" or "module" may refer to one or more passive and/or active components that are arranged to cooperate with one another to provide a desired function. The term "signal" may refer to at least one current signal, voltage signal, magnetic signal, or data/clock signal. The meaning of "a," "an," and "the" include plural references. The meaning of "in" includes "in" and "on."

The terms "substantially," "close," "approximately," "near," and "about," generally refer to being within +/−20% of a target value. Unless otherwise specified the use of the ordinal adjectives "first," "second," and "third," etc., to describe a common object, merely indicate that different instances of like objects are being referred to, and are not intended to imply that the objects so described must be in a given sequence, either temporally, spatially, in ranking or in any other manner.

For purposes of the embodiments, the transistors in various circuits, modules, and logic blocks are metal oxide semiconductor (MOS) transistors, which include drain, source, gate, and bulk terminals. The transistors also include Tri-Gate and FinFET transistors, Gate All Around Cylindrical Transistors, Tunneling FET (TFET), Square Wire, or Rectangular Ribbon Transistors or other devices implementing transistor functionality like carbon nano tubes or spintronic devices. MOSFET symmetrical source and drain terminals i.e., are identical terminals and are interchangeably used here. A TFET device, on the other hand, has asymmetric Source and Drain terminals. Those skilled in the art will appreciate that other transistors, for example, Bipolar junction transistors—BJT PNP/NPN, BiCMOS, CMOS, eFET, etc., may be used without departing from the scope of the disclosure.

FIG. 1 is a block diagram of an electronic device that enables air flow generation for scent output. The electronic device 100 may be, for example, a laptop computer, tablet computer, mobile phone, smart phone, a wearable headset, a smart headset, a smart glass or speaker system, among others. The electronic device 100 may also be a mobile computing device, such as a computing tablet, a mobile phone or smart-phone, a wireless-enabled e-reader, or other wireless mobile device. It will be understood that certain components are shown generally, and not all components of such a device are shown in computing device.

The electronic device 100 may include a central processing unit (CPU) 102 that is configured to execute stored instructions, as well as a memory device 104 that stores instructions that are executable by the CPU 102. The CPU may be coupled to the memory device 104 by a bus 106. Additionally, the CPU 102 can be a single core processor, a multi-core processor, a computing cluster, or any number of other configurations. Furthermore, the electronic device 100 may include more than one CPU 102. In embodiments, the CPU 102 may control one or more scent sources. The memory device 104 can include random access memory (RAM), read only memory (ROM), flash memory, or any other suitable memory systems. For example, the memory device 104 may include dynamic random access memory (DRAM).

In one embodiment, CPU 102 can include one or more physical devices, such as microprocessors, application processors, microcontrollers, programmable logic devices, or other processing means. The processing operations performed by CPU 102 include the execution of an operating platform or operating system on which applications and/or device functions are executed. The processing operations include operations related to I/O (input/output) with a human user or with other devices, operations related to power management, and/or operations related to connecting the electronic device 100 to another device. The processing operations may also include operations related to audio I/O and/or display I/O.

The electronic device 100 can also include an audio processing device 108. The audio processing device 108 can be configured to perform any number of audio processing operations, such as encoding or decoding audio data, retrieving audio files for rendering the audio on a sound system of the electronic device 100, audio equalization, and any other audio processing. In one embodiment, the audio processing device 108 is a component of an audio subsystem 110, which represents hardware (e.g., audio hardware and audio circuits) and software (e.g., drivers, codecs) components associated with providing audio functions to the computing device. Audio functions can include speaker and/or headphone output, as well as microphone input. Devices for such functions can be integrated into electronic device 100, or connected to the electronic device 100. Accordingly, the audio subsystem may be coupled with a speaker 112. In one embodiment, a user interacts with the electronic device 100 by providing audio commands that are received and processed by CPU 102.

The CPU 102 may also be linked through the bus 106 to a display interface 114 configured to connect with one or more display devices 116. The display devices 114 may include a display screen that is a built-in component the electronic device 100. Examples of such a computing device include mobile computing devices, such as cell phones, tablets, 2-in-1 computers, notebook computers or the like. The display device 116 may also include a computer monitor, television, or projector, among others, that is externally the electronic device 100.

The CPU 102 may be connected through the bus 106 to an input/output (I/O) device interface 130 configured to connect with one or more I/O devices 122. The I/O devices 122 may include, for example, a keyboard and a pointing device, wherein the pointing device may include a touchpad or a touchscreen, among others. The I/O devices 122 may be built-in components of the electronic device 00, or may be devices that are externally connected to the electronic device 100. For example, electronic device 100 can also include one or more user I/O devices 122, such as switches, buttons, a keyboard, a mouse, or trackball, among others. One of the input devices may be a touchscreen, which may be integrated with a display. The input devices 122 may be built-in components of the electronic device 100, or may be devices that are externally connected to the electronic device 100.

A storage device 124 is a physical memory such as a hard drive, an optical drive, a flash drive, an array of drives, or any combinations thereof. The storage device 124 can store user data, such as audio files, video files, audio/video files, and picture files, among others. The storage device 124 can also store programming code such as device drivers, software applications, operating systems, and the like. The programming code stored to the storage device 124 may be executed by the CPU 102, audio processor 108, or any other processors that may be included in the electronic device 100, such as a graphics processing unit (GPU).

The CPU 102 may be linked through the bus 106 to cellular hardware 126. The cellular hardware 126 may be any cellular technology, for example, the 4G standard (International Mobile Telecommunications-Advanced (IMT-Advanced) Standard promulgated by the International Telecommunications Union-Radio communication Sector (ITU-R)). Cellular hardware also refers generally to cellular network connectivity provided by wireless carriers, such as provided via GSM (global system for mobile communications) or variations or derivatives, CDMA (code division multiple access) or variations or derivatives, TDM (time division multiplexing) or variations or derivatives, or other cellular service standards. In this manner, electronic device 100 may access any network 132 without being tethered or paired to another device, where the network 122 is a cellular network.

The CPU 102 may also be linked through the bus 106 to WiFi hardware 128. The WiFi hardware is hardware according to WiFi standards (standards promulgated as Institute of Electrical and Electronics Engineers' (IEEE) 802.11 standards). The WiFi hardware 128 enables the wearable electronic device 100 to connect to the Internet using the Transmission Control Protocol and the Internet Protocol (TCP/IP), where the network 132 is the Internet. Accordingly, the wearable electronic device 100 can enable end-to-end connectivity with the Internet by addressing, routing, transmitting, and receiving data according to the TCP/IP protocol without the use of another device. Additionally, a Bluetooth Interface 130 may be coupled to the CPU 102 through the bus 106. The Bluetooth Interface 130 is an interface according to Bluetooth networks (based on the Bluetooth standard promulgated by the Bluetooth Special Interest Group). The Bluetooth Interface 130 enables the wearable electronic device 100 to be paired with other Bluetooth enabled devices through a personal area network (PAN). Accordingly, the network 132 may be a PAN. Examples of Bluetooth enabled devices include a laptop computer, desktop computer, ultrabook, tablet computer, mobile device, or server, among others. Accordingly, the electronic device 100 includes wireless connectivity that can include personal area networks (such as Bluetooth, Near Field, etc.), local area networks (such as Wi-Fi), and/or wide area networks (such as WiMax), or other wireless communication. The electronic device 100 may also include network interface within to connect with the network 132 such as a wireless interface so that a system embodiment may be incorporated into a wireless device, for example, cell phone or personal digital assistant.

The block diagram of FIG. 1 is not intended to indicate that the computing device 100 is to include all of the components shown in FIG. 1. Rather, the computing system 100 can include fewer or additional components not illustrated in FIG. 1 (e.g., sensors, power management integrated circuits, additional network interfaces, etc.). The computing device 100 may include any number of additional components not shown in FIG. 1, depending on the details of the specific implementation. Furthermore, any of the functionalities of the CPU 102 may be partially, or entirely, implemented in hardware and/or in a processor. For example, the functionality may be implemented with an application specific integrated circuit, in logic implemented in a processor, in logic implemented in a specialized graphics processing unit, or in any other device.

Figure 2:
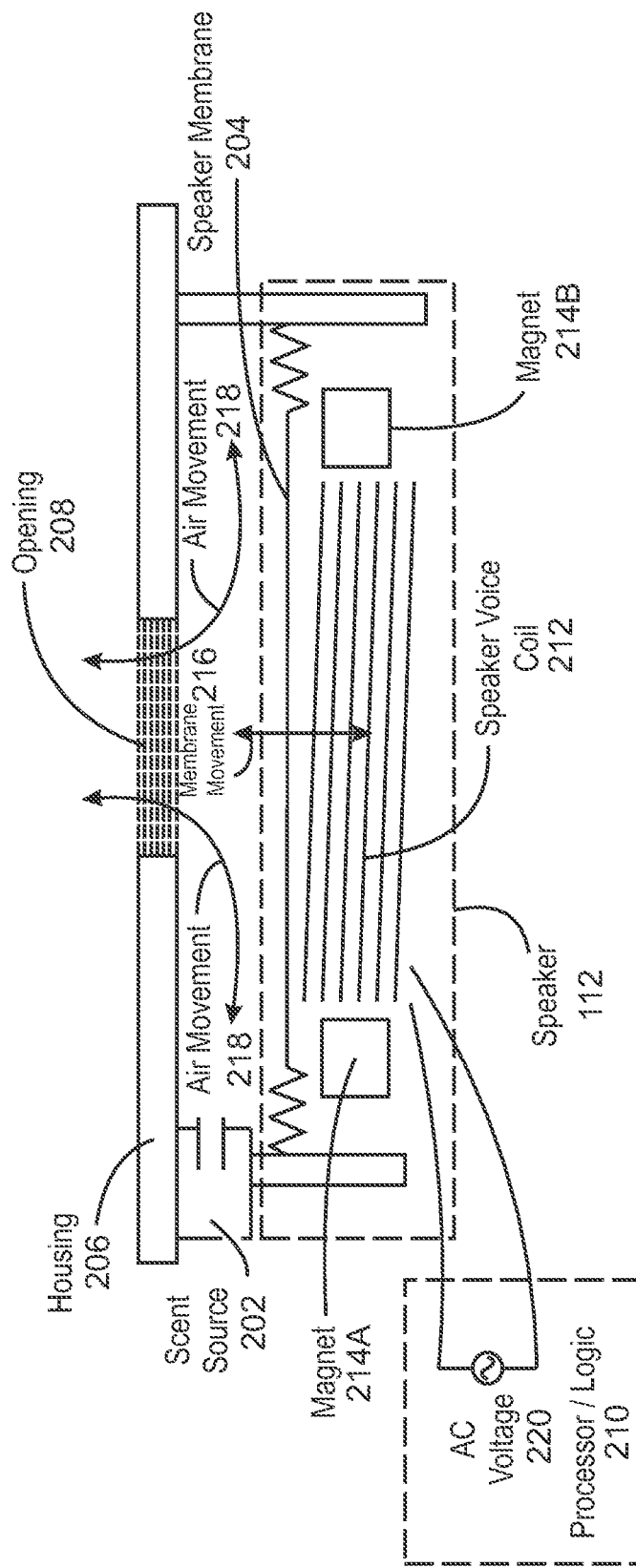
FIG. 2 is an illustration of a system 200 including a speaker with scent output of an electronic device.

FIG. 2 is an illustration of a system 200 including a speaker with scent output of an electronic device. The speaker 112 is positioned near a scent source 202 and a speaker membrane 204 that work together to control the generation of scent output from the scent source. Although one scent source is illustrated, the scent source may be used to produce a plurality of scents. Additionally, more than once scent source may be present in the system. The system 200 also includes a housing 206, opening 208, and a processor 210. The opening 208 may be any area that enables air to move from inside the housing 206 to outside the housing 206. In embodiments, the opening 208 is completely clear of any coverings. However, as illustrated, the opening 208 may be a breathable material, such as a screen, to enable air movement while protecting the speaker 112 and other components near the opening.

The speaker 112 includes the speaker membrane 204, speaker voice coil 212 and magnets 214A and 214B on either side of the speaker voice coil 212. In embodiments, speaker membrane 204 is operable to vibrate to generate sound. Any suitable material may be used for forming speaker membrane 204. The vibrations caused by the membrane movement 216 causes air movement 218 through the opening 208 from the area within housing 206 near the speaker membrane. As discussed below, the membrane movement is sufficient to carry scents from the scent source 202 through the opening 208. The air movement causes scents at the scent source 203 to the transported outside of the housing 206.

In embodiments, the sensed scent source may be controlled by a processor 210. For example, the processor 210 may control the opening and closing of the scent source, which allows the scent to be output in a coordinated fashion. In embodiments, the when the speaker membrane 204 is active, the system 200 is able to output scents from the scent source. The output of scents can be coordinated with sound produced by the speaker 112. The output of scents can also be coordinated with the various applications, such as gaming, social networking, word processing, and any other computer activities.

As noted above, scent output occurs when the speaker membrane is active. Thus, scent output can occur even when no sound is emitted from the speaker 112. For example, when the speaker 112 is not operational for its primary purpose (e.g., for making sound/music), the processor 210 may cause the speaker 112 to be driven by a very low frequency AC voltage signal 220 (e.g., 10 Hz). This AC voltage 220 at a low frequency applied to the speaker 112 does not cause the speaker to generate audio detectable by human ears. Rather, the low frequency cause enough vibrations of the speaker membrane 204 to cause air movement 216 such that scents are moved from the scent source 202 through the opening 208.

While FIG. 2 illustrates controlling the vibration frequency of speaker membrane 204 to manage airflow, the airflow can be managed by other electromechanical devices. For example, in embodiments, an electromechanical device is a cooling fan or a blower, and the processor 210 controls the speed of the cooling fan or blower to be slow enough for air exchange, for proper operation of the scent source 202, but not fast enough to cause noise audible to a human.

Figure 3:
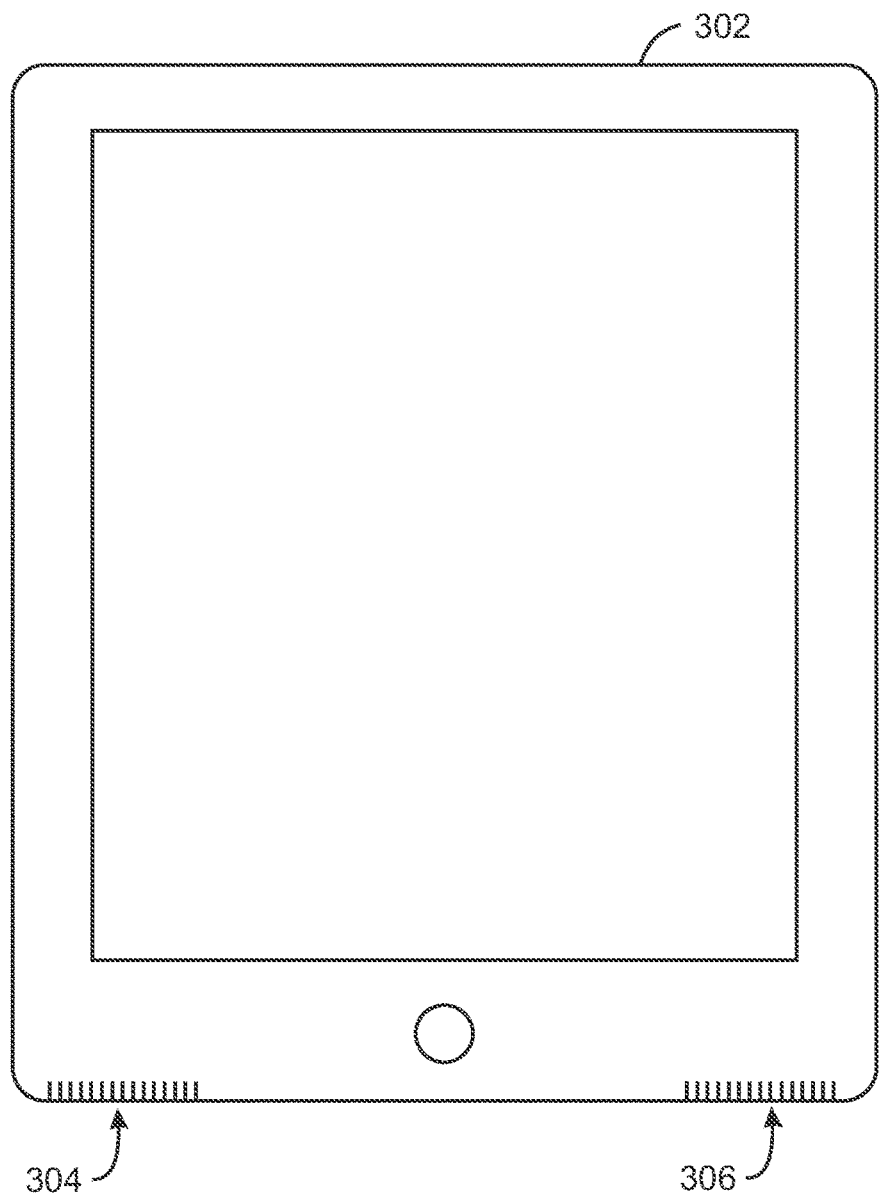
FIG. 3 is an illustration of a tablet device 300 that includes a scent source and speaker.

FIG. 3 is an illustration of a tablet device 300 that includes a scent source and speaker. The scent source may be a scent source 202 and the speaker may be a speaker 112 as described above. In embodiments, the tablet 300 includes a system 200 (FIG. 2). As illustrated, the tablet includes an exterior housing 302. The housing also includes openings 304 and 306. In embodiments, each of the openings 304 and 306 corresponds to a scent source and a speaker. The openings 304 and 306 may also share a scent source and a speaker. Moreover, the openings 304 and 306 may correspond to a scent source controlled by a separate microcontroller, or the openings 304 and 306 may correspond to a scent source jointly controlled by a single processor 210 (FIG. 2) or the CPU 102.

In examples, a typical speaker used in many smartphones and tablets is 13 mm×18 mm size (width×length). The moving membrane of the speaker can be approximately 11 mm×16 mm. An amplitude of the movement created by the speaker membrane may be 0.6 mm. As used herein, the amplitude refers to a peak-to-peak measurements of the vibrations that occur at the speaker membrane. In examples, the air movement during one cycle of speaker membrane movement is approximately 106 cubic millimeters. One cycle refers to one complete vibration of the speaker membrane. Continuing with the previous example, the cavity near the speaker membrane can measure approximately 300-400 cubic millimeters. A single speaker cycle from the minimum to the maximum speaker membrane displacement will exchange approximately 25-30% of the front cavity air volume. This results in the movement of the scent source outside of the device housing.

If the speaker operates at, for example, 100 Hz, we could completely pump the scent out of the speaker system in a fraction of a second, in the above example it would take 100 ms to output about 98% of the scent. In embodiments, the speaker membrane frequency corresponds to the AC signal frequency. Accordingly, a speaker operating a 100 Hz has a membrane that is vibrating at 100 Hz. While the speaker size has been detailed as an example, each speaker system can be adjusted to take advantage of the speaker membrane vibrations in order to produce scent output.

Figure 4:
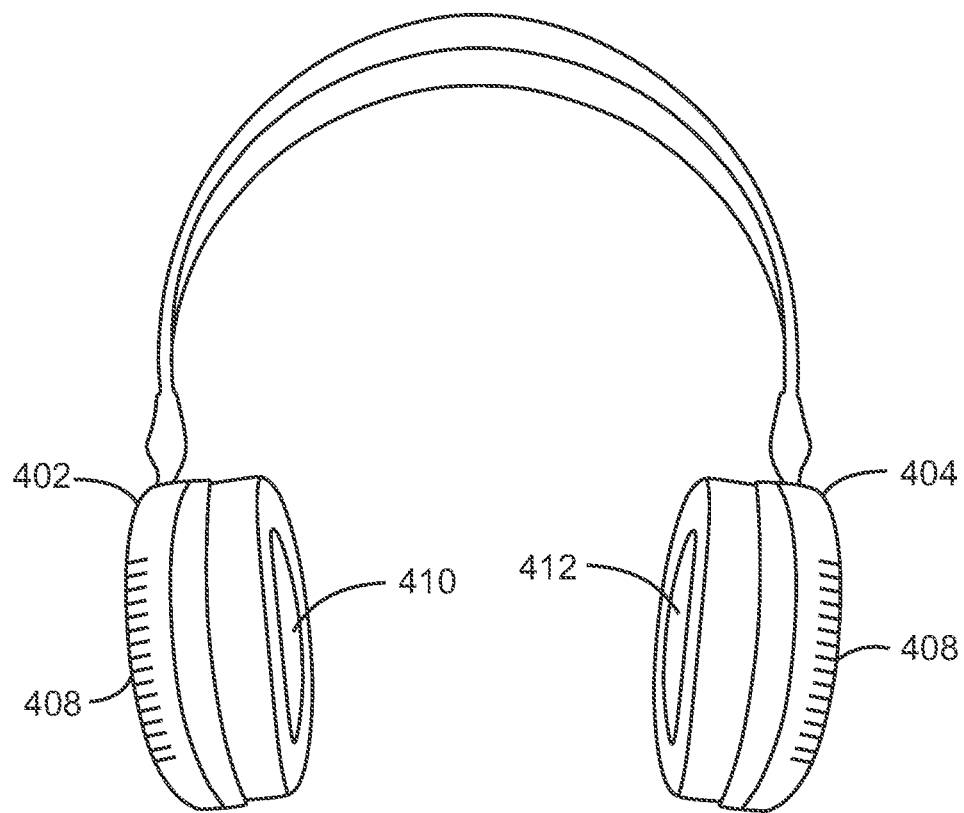
FIG. 4 is an illustration of a headset device 400 that includes a scent source and speaker.

FIG. 4 is an illustration of a headset device 400 that includes a scent source and speaker. The scent source may be a scent source 202 and the speaker may be a speaker 112 as described above. In embodiments, the headset device 400 includes a system 200 (FIG. 2). As illustrated, the headset device 400 includes an exterior housings 402 and 404 for each speaker. The housing 402 also includes opening an opening 406. The housing 404 also include opening an opening 408. In embodiments, each of the openings 406 and 408 corresponds to a scent source and a speaker. Moreover, the openings 406 and 408 may correspond to a scent source controlled by a separate microcontroller, or the openings 406 and 408 may correspond to a scent source jointly controlled by a single processor 210 (FIG. 2) or the CPU 102.

In examples, sound is produced at ear locations 410 and 412. When the headset device 400 is secured to the ears of a user, air cannot flow freely towards the ears. Accordingly, openings 406 and 408 enable air from the speaker membrane to move outside of the housings 402 and 404, respectively. While the openings are illustrated as positioned on the backside of the housings 402 and 404, the openings can be located at any position along the housings. Depending on the size and shape of the housings, a different position for the openings may be desired.

Figure 5:
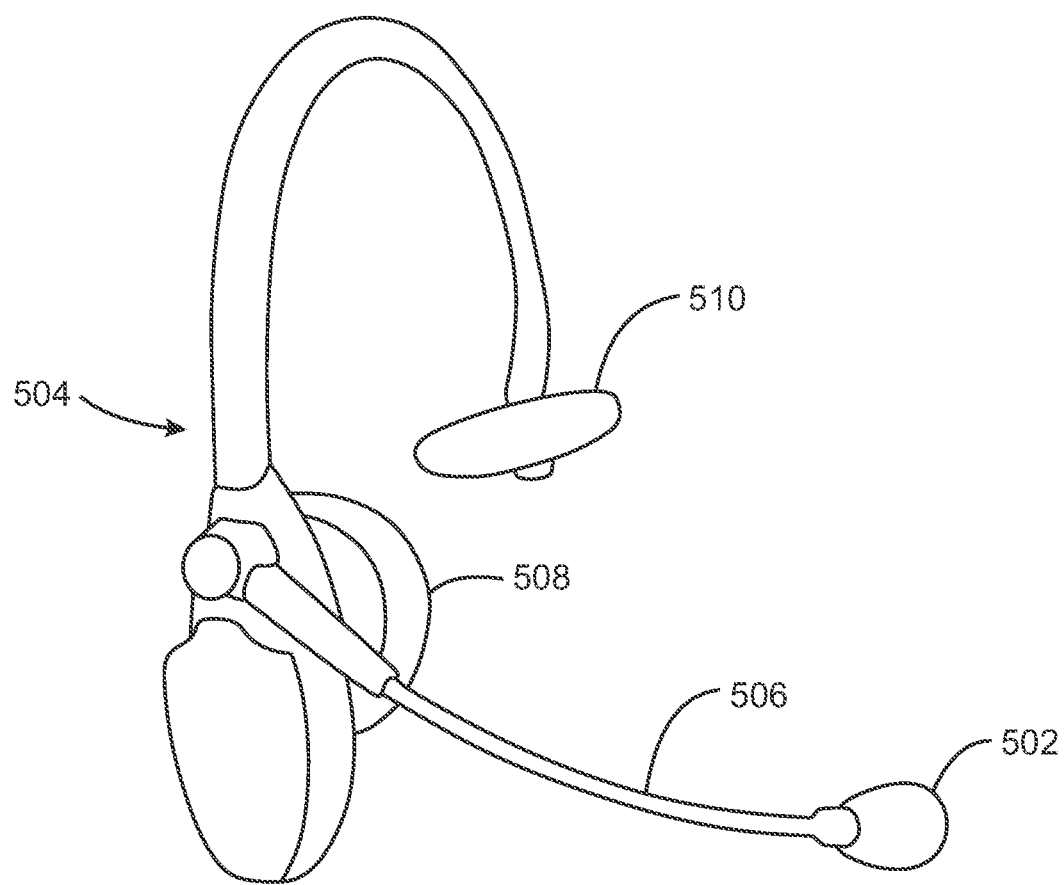
FIG. 5 is an illustration of a headset device 500 with a microphone that includes a scent source and speaker.

FIG. 5 is an illustration of a headset device 500 with a microphone that includes a scent source and speaker. The scent source may be a scent source 202 and the speaker may be a speaker 112 as described above. In embodiments, the headset device 500 includes a system 200 (FIG. 2). As illustrated, the headset device 500 includes a bulb 502 connected to a housing 504 via an extension 506. The bulb may include a microphone for capturing audio as well as a system 200 for scent output. The housing 504 is also connected to a speaker 508 and a guide 510. While one side of the headset device 500 is illustrated as having a guide 510, the guide 510 may also be a speaker 510. The speaker system 200 included in the bulb 502 may not produce sound. However, a membrane can be activated at a very low frequency in order to disperse scents at a location near the nose of a user. In embodiments, the microphone included in the bulb 502 can be modified to create air flow in order to disperse scents outside of the bulb 502.

Figure 6:
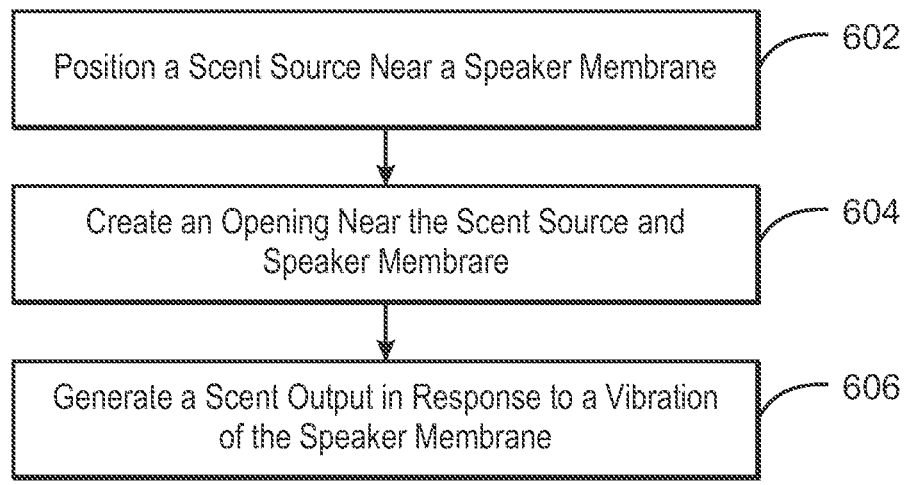
FIG. 6 is a process flow diagram of a method 600 for generating air flow for scent output.

FIG. 6 is a process flow diagram of a method 600 for generating air flow for scent output. At block 602, a scent source is positioned near a speaker membrane. At block 604, an opening is created near the scent source and speaker membrane. The opening may be a screen that protects the speaker membrane, while allowing air to flow through the opening. At block 606, a scent output is generated in response to a vibration of the speaker membrane.

The speaker membrane is considered active when the vibrations occur. In examples, vibration of the speaker membrane causes air to flow away from the speaker membrane, where the air includes scent output that can be observed by a user. The scent output can coordinate with user activity, such as gaming and social networking. For example, scent output can be released at certain points in a game. As another example, a user working at an electronic device with a scent system or coupled with a scent output system can observe scents that are coordinated with work flow, work levels, or other work indicators as calculated, scent output can be released. In such an example, the scent output may include calming scents or scents to increase the user's productivity.

Although the blocks in the flowchart with reference to FIG. 6 are shown in a particular order, the order of the actions can be modified. Thus, the illustrated embodiments can be performed in a different order, and some actions/blocks may be performed in parallel. The numbering of the blocks presented is for the sake of clarity and is not intended to prescribe an order of operations in which the various blocks must occur. Additionally, operations from the various flows may be utilized in a variety of combinations.

Figure 7:
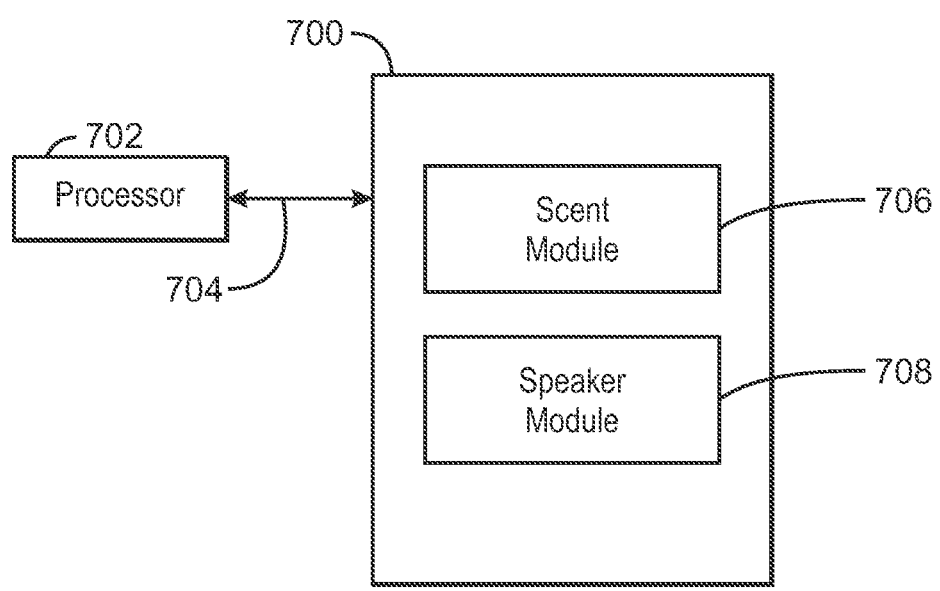
FIG. 7 is a block diagram showing a medium 700 that contains logic for the generation of scent output.

FIG. 7 is a block diagram showing a medium 700 that contains logic for the generation of scent output. The medium 700 may be a computer-readable medium, including a non-transitory medium that stores code that can be accessed by a processor 702 over a computer bus 704. For example, the computer-readable medium 700 can be volatile or non-volatile data storage device. The medium 700 can also be a logic unit, such as an Application Specific Integrated Circuit (ASIC), a Field Programmable Gate Array (FPGA), or an arrangement of logic gates implemented in one or more integrated circuits, for example.

The medium 700 may include modules 706-708 configured to perform the techniques described herein. For example, a scent module 706 may be configured to release scents to be pumped outside of a housing via an opening. A speaker module 708 may be configured to generate an air flow to push the scent outside of a housing via an opening. The scent may be pumped outside of the opening via a vibrating scent membrane. In embodiments, the modules 706-708 may be modules of computer code configured to direct the operations of the processor 702.

The block diagram of FIG. 7 is not intended to indicate that the medium 700 is to include all of the components shown in FIG. 7. Further, the medium 700 may include any number of additional components not shown in FIG. 7, depending on the details of the specific implementation.

Example 1

A wearable device is described herein. The wearable device comprises a scent system, a speaker, and an output channel. The scent system and the speaker share the output channel, and the speaker is to move air to release scent from the device.

In examples, the speaker may force air through the output channel to move the scent. The scent source may be electrically controlled. The wearable device may include a plurality of scent systems. In examples, moving the scent is may occur during a normal air exchange by the speaker. A low frequency voltage may be provide air movement without providing any sound. Moreover, the output channel may be directed to the nose of a user. In examples, scent system may be to be refilled. The scent system may comprise a plurality of scents.

Example 2

A method for generating air flow for scent output is described herein. The method comprises positioning a scent source near a speaker membrane and creating an opening near the scent source and speaker membrane. The method also comprises generating a scent output in response to a vibration of the speaker membrane.

In examples, the speaker membrane may be active during the vibration. The vibration of the speaker membrane may cause air to flow away from the speaker membrane. The air flow away from the speaker membrane may include the scent output. Moreover, the speaker membrane may produce sound during the vibration. The speaker membrane may also produce no sound during the vibration. In examples, the speaker membrane may vibrate at a very low frequency. The speaker membrane can act as an air pump during speaker vibrations. The speaker membrane may be a diaphragm. The scent source may be controlled in a coordinated fashion with a speaker including the speaker membrane. The opening may be a screen that may protect the speaker membrane.

Example 3

A system for generating air flow for scent output is described herein. The system comprises a speaker, a scent source, and a processor. The processor is communicatively coupled to the scent source and speaker, wherein when the processor is to execute instructions, the processor is to configure the scent source for scent output and cause vibrations of a membrane of the speaker, where an airflow is to transport a scent from the scent source as a result of the vibrations.

In examples, the vibrations may cause the membrane to act as an air pump. The configuration of the scent source may cause the scent to be available for transport. The scent source may comprise a plurality of scents. A low frequency voltage may provide air movement without providing any sound. Moreover, scent output and vibrations of the membrane may be coordinated according to user activity. A second air mover may transport a scent from the scent source. In examples, the second air mover may be a fan. The second air mover may induce electromechanical air movement. The second air mover may be a haptic actuator.

Example 4

An apparatus for generating air flow for scent output. The apparatus comprises a scent system, a means to transport scent from the scent system, and an output channel. The scent system and the means to transport scent from the scent system share the output channel, and the speaker is to move air to release scent from the device.

In examples, the means to transport scent from the scent system can force air through the output channel to move the scent. The scent source may be electrically controlled. The device may comprise a plurality of scent systems. Moving the scent may occur during a normal air exchange by the means to transport scent from the scent system. A low frequency voltage may be provide air movement without providing any sound. In examples, output channel may be directed to the nose of a user. The scent system may be refilled. The apparatus may comprise a plurality of scent systems.

Example 5

A system for generating air flow for scent output is described herein. The system comprises an air mover, a scent source, and a processor. The processor is communicatively coupled to the scent source and the air mover, wherein when the processor is to execute instructions, the processor is to configure the scent source for scent output and to operate the air mover, wherein an airflow from the air mover is to transport a scent from the scent source as a result of the operation.

In examples, the air mover may induce electromechanical air movement. The air mover may induce air movement via a haptic effect. The air mover may be a fan. Additionally, in examples, the air mover may induce air movement via a piezoelectric actuator. The air mover may induce air movement via a vibrating motor. The configuration of the scent source may cause the scent to be available for transport. The scent source may comprise a plurality of scents. A second air mover may transport a scent from the scent source.

Some embodiments may be implemented in one or a combination of hardware, firmware, and software. Some embodiments may also be implemented as instructions stored on the tangible, non-transitory, machine-readable medium, which may be read and executed by a computing platform to perform the operations described. In addition, a machine-readable medium may include any mechanism for storing or transmitting information in a form readable by a machine, e.g., a computer. For example, a machine-readable medium may include read only memory (ROM); random access memory (RAM); magnetic disk storage media; optical storage media; flash memory devices; or electrical, optical, acoustical or other form of propagated signals, e.g., carrier waves, infrared signals, digital signals, or the interfaces that transmit and/or receive signals, among others.

An embodiment is an implementation or example. Reference in the specification to "an embodiment," "one embodiment," "some embodiments," "various embodiments," or "other embodiments" means that a particular feature, structure, or characteristic described in connection with the embodiments is included in at least some embodiments, but not necessarily all embodiments, of the present techniques. The various appearances of "an embodiment," "one embodiment," or "some embodiments" are not necessarily all referring to the same embodiments.

Not all components, features, structures, characteristics, etc. described and illustrated herein need be included in a particular embodiment or embodiments. If the specification states a component, feature, structure, or characteristic "may", "might", "can" or "could" be included, for example, that particular component, feature, structure, or characteristic is not required to be included. If the specification or claim refers to "a" or "an" element, that does not mean there is only one of the element. If the specification or claims refer to "an additional" element, that does not preclude there being more than one of the additional element.

It is to be noted that, although some embodiments have been described in reference to particular implementations, other implementations are possible according to some embodiments. Additionally, the arrangement and/or order of circuit elements or other features illustrated in the drawings and/or described herein need not be arranged in the particular way illustrated and described. Many other arrangements are possible according to some embodiments.

In each system shown in a figure, the elements in some cases may each have a same reference number or a different reference number to suggest that the elements represented could be different and/or similar. However, an element may be flexible enough to have different implementations and work with some or all of the systems shown or described herein. The various elements shown in the figures may be the same or different. Which one is referred to as a first element and which is called a second element is arbitrary.

It is to be understood that specifics in the aforementioned examples may be used anywhere in one or more embodiments. For instance, all optional features of the computing device described above may also be implemented with respect to either of the methods or the computer-readable medium described herein. Furthermore, although flow diagrams and/or state diagrams may have been used herein to describe embodiments, the techniques are not limited to those diagrams or to corresponding descriptions herein. For example, flow need not move through each illustrated box or state or in exactly the same order as illustrated and described herein.

The present techniques are not restricted to the particular details listed herein. Indeed, those skilled in the art having the benefit of this disclosure will appreciate that many other variations from the foregoing description and drawings may be made within the scope of the present techniques. Accordingly, it is the following claims including any amendments thereto that define the scope of the present techniques.

What is claimed is:

1. A wearable device, comprising:
   a scent system;
   a speaker;
   an output channel, wherein the scent system and the speaker share the output channel, and the speaker is to move air to release scent from the device, wherein a membrane of the speaker is operable to produce audible sound and causes air movement to move air by generating an electromechanically induced air movement to release scent from the device.

2. The wearable device of claim 1, wherein the membrane of the speaker forces air through the output channel to move the scent through the output channel.

3. The wearable device of claim 1, wherein the scent system-is electrically controlled.

4. The wearable device of claim 1, comprising a plurality of scent systems.

5. The wearable device of claim 1, wherein releasing the scent is to occur during a normal air exchange by the speaker.

6. The wearable device of claim 1, wherein a low frequency voltage applied to the speaker is to provide air movement without providing any sound from the membrane of the speaker.

7. The wearable device of claim 1, wherein the output channel is directed to the nose of a user.

8. The wearable device of claim 1, wherein the scent system is to be refilled.

9. The wearable device of claim 1, comprising a plurality of scents within the scent system.

10. A method for generating air flow for scent output, comprising:
    positioning a scent source near a speaker membrane;
    creating an opening near the scent source and speaker membrane; and
    generating a scent output in response to a vibration of the speaker membrane, wherein the speaker membrane is operable to produce audible sound and causes air movement to move air by generating an electromechanically induced air movement to release scent from the device.

11. The method of claim 10, wherein the speaker membrane is active during the vibration.

12. The method of claim 10, wherein the vibration of the speaker membrane causes air to flow away from the speaker membrane.

13. The method of claim 10, wherein air flow away from the speaker membrane includes the scent output.

14. A system for generating air flow for scent output, comprising:
    a speaker;
    a scent source;
    a processor communicatively coupled to the scent source and speaker, wherein when the processor is to execute instructions, the processor is to configure the scent source for scent output and cause low frequency vibrations of a speaker membrane that is operable to produce audible sound, where an airflow is generated from the low frequency vibrations of the speaker membrane via an electromechanically induced air movement and is to transport a scent from the scent source via the airflow generated by the speaker membrane as a result of the vibrations.

15. The system of claim 14, wherein the vibrations cause the speaker membrane to act as an air pump.

16. The system of claim 14, wherein the configuration of the scent source is to cause the scent to be available for transport.

17. The system of claim 14, wherein the scent source comprises a plurality of scents.

18. A system for generating air flow for scent output, comprising:
    an air mover;
    a scent source;
    a processor communicatively coupled to the scent source and the air mover, wherein when the processor is to execute instructions, the processor is to configure the scent source for scent output and to operate the air mover, wherein an airflow from the air mover is generated at least in part by a vibration of a speaker membrane that is operable to produce audible sound and is to transport a scent from the scent source via the airflow generated by the speaker membrane via an electromechanically induced air movement.

19. The system of claim 18, wherein the air mover induces air movement via a haptic effect.

20. The system of claim 18, wherein the air mover is a fan.

21. The system of claim 18, wherein the air mover induces air movement via a piezoelectric actuator.

22. The system of claim 18, wherein the air mover induces air movement via a vibrating motor.

23. The system of claim 18, wherein the configuration of the scent source is to cause the scent to be available for transport.

* * * * *